United States Patent
Pusterla et al.

(10) Patent No.: US 7,067,800 B2
(45) Date of Patent: Jun. 27, 2006

(54) METHOD FOR MEASURING THE CONCENTRATION OF IMPURITIES IN NITROGEN, HYDROGEN AND OXYGEN BY ION MOBILITY SPECTROMETRY

(75) Inventors: Luca Pusterla, Milan (IT); Marco Succi, Milan (IT); Antonio Bonucci, Milan (IT); Robert Stimac, Palm Beach Gardens, FL (US)

(73) Assignee: Saes Getters S.p.A., Lainate (IT)

( * ) Notice: Subject to any disclaimer, the term of this patent is extended or adjusted under 35 U.S.C. 154(b) by 23 days.

(21) Appl. No.: 10/457,171

(22) Filed: Jun. 9, 2003

(65) Prior Publication Data

US 2003/0209664 A1    Nov. 13, 2003

Related U.S. Application Data

(63) Continuation of application No. PCT/IT01/00629, filed on Dec. 21, 2001.

(30) Foreign Application Priority Data

Dec. 22, 2000    (IT)    ............ MI2000A2830

(51) Int. Cl.
*B01D 59/44* (2006.01)
(52) U.S. Cl. ............ 250/282; 250/287; 702/24
(58) Field of Classification Search ........ 250/288, 250/286, 287, 282
See application file for complete search history.

(56) References Cited

U.S. PATENT DOCUMENTS

| | | | | |
|---|---|---|---|---|
| 5,457,316 A | * | 10/1995 | Cohen et al. | ...... 246/321 |
| 5,955,886 A | | 9/1999 | Cohen et al. | |
| 6,229,143 B1 | | 5/2001 | Wernlund | |
| 6,639,214 B1 | * | 10/2003 | Ketkar et al. | ...... 250/287 |

FOREIGN PATENT DOCUMENTS

EP    1 154 268 A2    11/2001
WO    WO 00/52432 A3    9/2000

OTHER PUBLICATIONS http://www.scottsemicon.com/mixes/moxygen.html, p. 1, Dec. 12, 2000.*
http://www.scottsemicon.com/mixes/mhydrogen.html, p. 1, Dec. 12, 2000.*

* cited by examiner

*Primary Examiner*—Nikita Wells
*Assistant Examiner*—Philip A Johnston
(74) *Attorney, Agent, or Firm*—Akin Gump Strauss Hauer & Feld, LLP (57) ABSTRACT

A method for the quantitative analysis of the impurities content in nitrogen, hydrogen or oxygen by means of ion mobility spectrometry is described. The method involves using pure argon or a mixture, having no impurities, containing argon and the gas to be analyzed, as a counterflow gas in the separation zone of the ion mobility spectrometer.

3 Claims, 8 Drawing Sheets

METHOD FOR MEASURING THE CONCENTRATION OF IMPURITIES IN NITROGEN, HYDROGEN AND OXYGEN BY ION MOBILITY SPECTROMETRY

CROSS-REFERENCE TO RELATED APPLICATIONS

This application is a continuation of International Application No. PCT/IT01/00629 filed Dec. 21, 2001, which was published in the English language on Jul. 4, 2002 under International Publication No. WO 02/052255A1, the disclosure of which is incorporated herein by reference.

BACKGROUND OF THE INVENTION

The present invention relates to a method for measuring the concentration of impurities in nitrogen, hydrogen and oxygen by means of ion mobility spectrometry.

Nitrogen, hydrogen and oxygen are some of the gases used as reaction media, or as the actual reagents, in the integrated circuits industry. It is known that in the production of these devices the purity of the reagents is of utmost importance; as a matter of fact, contaminants possibly present in the reagents or in the reaction environment can be incorporated into the solid state devices, thus altering the electrical properties thereof and giving rise to production wastes. The specifications on the purity of the gases employed in production can vary from one manufacturer to another and depend on the particular process in which the gas is employed. Generally, a gas is considered to be acceptable for production when its impurities content is not higher than 10 ppb (parts per billion); preferably, the content in impurities is lower than 1 ppb. As a result, it is important to be able to measure extremely low concentrations of impurities in gases in a precise and reproducible way.

A technique which can be used for this purpose is ion mobility spectrometry, known in the field with the abbreviation IMS; the same abbreviation is also used for the instrument with which the technique is carried out, in this case indicating "Ion Mobility Spectrometer." The interest for this technique derives from its very high sensitivity, associated with the limited size and cost of the instrument. By operating under appropriate conditions it is possible to sense species in the gas or vapor phase in a gaseous medium in quantities on the order of picograms (pg, $10^{-12}$ grams), or in concentrations on the order of parts per trillion (ppt, equivalent to one molecule of analyzed substance for every $10^{-12}$ gas molecules of the sample). IMS instruments and methods of analysis in which they are employed are described, for example, in U.S. Pat. Nos. 5,457,316 and 5,955,886 in the name of the U.S. company PCP Inc, and in U.S. Pat. No. 6,229,143, in the name of the Applicant.

An IMS instrument is essentially formed of a reaction zone, a separation zone and a collector of charged particles.

In the reaction zone takes place the ionization of the sample comprising the gases or vapors to be analyzed in a carrier gas, commonly by means of beta-radiation emitted by $^{63}$Ni. The ionization takes place mainly on the carrier gas with the formation of the so-called "reagent ions," whose charge is then distributed onto the species present depending on their electron or proton affinities or their ionization potentials.

The reaction zone is divided from the separation zone by a grid which, when kept at a suitable potential, prevents the ions produced in the reaction zone from entering into the separation zone. The moment when the grid potential is annulled, thus allowing the ions to enter into the separation zone, is the "time zero" of the analysis.

The separation zone comprises a series of electrodes which create an electric field such that the ions are carried from the reaction zone toward a collector. In this zone, which is kept at atmospheric pressure, a gas flow having opposite direction with respect to that of the ions' movement is present. Commonly, the counterflow gas, defined in the field as "drift gas," is an extremely pure gas corresponding to the gas whose content of impurities is to be determined. As an example, in an IMS analysis for determining the content of impurities in nitrogen, the drift gas is normally pure nitrogen. The velocity of motion of the ions depends on the electric field and on the cross-section of the same ions in the gaseous medium, so that different ions take different times for crossing the separation zone and for reaching the particle collector. The time passed from the "time zero" to the time of arrival on the particle collector is called "time of flight." The collector is connected to a signal processing system, which transforms the current values sensed as a function of time into a final graph in which peaks corresponding to the various ions as a function of the "time of flight" are shown. From the determination of this time and knowing the test conditions, it is possible to determine the presence of the substances which are the object of the analysis. From the peak areas with suitable computation algorithms, it is also possible to calculate the concentrations of the corresponding species.

In spite of its conceptual simplicity, the application of the technique involves some difficulties in the interpretation of the analysis results. This is due firstly to the fact that the net charge distribution among the various species present is the result of equilibria which depend on various factors, with the result that the peaks corresponding to one impurity can be modified in intensity, or even disappear, depending on the presence of other impurities. The book "Ion Mobility Spectrometry" by G. A. Eiceman and Z. Karpas, published in 1994 by CRC Press, can be referred to for an illustration of the (rather complex) charge transfer principles which are the base of the technique. Further, keeping constant the chemical composition of the gas, the results depend on the analysis parameters, such as the electric field applied in the separation zone, the flow rate of the gas which has to be analyzed, and the flow rate of the drift gas.

As a consequence of these phenomena, the shape of the graph resulting from an IMS analysis is strongly dependent on the analysis conditions. The computation algorithms used for interpreting the analysis results are based on the deconvolution of the complete graph and on the relative measure of the areas of all the peaks present. The best results are obtained when each ionic species present gives rise to a separate peak in the graph. The analysis is still possible, although with greater difficulties, when the time of flight of a limited number of different species are similar, giving rise to a few peaks derived from the superimposition of singular peaks; in these cases it is necessary to resort to hypotheses about how the peak area is to be shared among the different species, with the risk however of introducing errors in the analysis. Finally, the IMS analysis (also the qualitative one) is impossible when large superimpositions between peaks corresponding to different species occur.

Because of the complexity of the phenomena in play, there is no standard method for applying the IMS technique, and each analysis has to be studied separately in order to define the conditions which allow for a good separation of all the peaks corresponding to the different species which can be present in the gas under analysis.

BRIEF SUMMARY OF THE INVENTION

The object of the present invention is to provide a method for measuring the concentration of impurities in nitrogen, hydrogen and oxygen by means of ion mobility spectrometry. The method comprises employing as a counterflow gas in a separation zone of an ion mobility spectrometer pure argon or a mixture of argon and the gas to be analyzed; the mixture contains substantially no impurities and is (a) an argon nitrogen mixture comprising at least 80% by volume of argon based on a total volume of the mixture; or (b) an argon/hydrogen or argon/oxygen mixture comprising at least 50% by volume of argon.

In particular, with the method according to the invention the best results are obtained by using a ratio between the flow rate of argon (or the argon rich mixture) and the flow rate of the gas under analysis which varies according to the nature of the latter.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The invention will be described in the following with reference to FIGS. 1 to 8, which show the results of IMS analyses carried out according to the procedure of the invention and of comparative analyses, carried out in conditions not according to the invention.

The standard way to carry out an IMS analysis requires the use of a drift gas which is the same gas (obviously pure) as the main gas in the sample whose impurity content is to be determined.

On the contrary, the inventors have found that, in the case of the analysis of impurities in nitrogen, hydrogen or oxygen, the use of a drift gas of pure argon, or of suitable argon/nitrogen, argon/hydrogen or argon/oxygen mixtures containing no impurities, allows the quantitative analysis to be carried out with good and reproducible results. These suitable mixtures have been found to be an argon/nitrogen mixture containing at least 80% by volume of argon, based on the total volume of the mixture, for the analysis of impurities in nitrogen, or argon/hydrogen or argon/oxygen mixtures containing at least 50% by volume of argon for the analyses of impurities in hydrogen and oxygen, respectively.

The use of argon or of argon-rich mixtures allows one to obtain graphs in which the peaks corresponding to the different species are separated, thus enabling a reliable quantitative analysis as discussed above. On the contrary, by using as a drift gas the same gas whose impurities content is to be determined, graphs with one or more superimposed peaks are generally obtained. For the sake of brevity, in the remainder of this text, reference will be made to the use of argon alone as the drift gas, meaning however also the above defined argon-rich mixtures.

It has also been found that for the purposes of the invention it is preferable that the ratio between the flow rate of argon (drift gas) and the flow rate of the gas whose impurities content is to be determined be different according to the chemical nature of the gas under analysis. In particular, this ratio is preferably equal to at least 10 in the case of hydrogen, at least 5 in the case of nitrogen, and between 0.3 and 1.5 or between 6 and 10 in the case of oxygen. The inventors have found that, in the case of hydrogen and nitrogen, these flow rate ratios between the drift gas and the gas under analysis allow the best separation of the different peaks to be obtained. In the case of oxygen, a ratio lower than 1 between the flow rate of the drift gas and the gas under analysis gives rise to "noises" in the signal, such as irregularities in the shapes of the peaks, which decrease their area (decreasing the sensitivity of the analysis), making the determination of the same area much more complex, and consequently possibly introducing errors in the quantitative analysis.

On the other hand, too high a ratio between the flow rate of argon and that of the gas to be analyzed has the effect of diluting the latter, with the risk of diminishing the method sensitivity.

As a compromise between the opposed needs illustrated above, the ratio between the flow rate of argon and of the gas under analysis is preferably maintained at a relatively low value; this ratio will be thus preferably be between 15 and 25 in the case of hydrogen, between 5 and 10 in the case of nitrogen, and preferably about 0.5 or about 8 in the case of oxygen.

The invention will be further illustrated by the following non-limiting examples. The examples have the purpose of demonstrating how, by operating under the invention conditions, it is possible to obtain by IMS analysis graphs which have a better peak separation with respect to the graphs obtained under condition which are not according to the invention. As discussed above, using the conditions according to the invention, graphs with separated peaks can be more easily interpreted, giving rise to more reliable analysis results. For the tests, suitable mixtures were prepared by adding selected impurities to the base gas. In particular, carbon dioxide ($CO_2$) is added to hydrogen, oxygen to nitrogen, and water to oxygen.

The test results are reported in graphs showing peaks as a function of the time of flight of the corresponding ions measured in milliseconds (ms); the peaks have areas corresponding to the concentrations of the different ions. These ions are generally complex species, which may comprise one, two or more molecules of the ionized gas, possibly associated to one or more molecules of the carrier gas (this phenomenon is also referred to in the field as "clustering"). For the sake of simplicity, the main peaks in the figures are identified with the formulas of the molecular species to which they are ascribed instead of with the formulas of the corresponding actual ions. The peak intensities are given in volts (V). The transformation of the current directly measured by the collector (the number of ions which collide on the collector per unit of time) into the value in volts, reported in the graphs on the ordinate axes, is performed by the instrument electronics. The ionization of the sample is carried out by a radioactive source of $^{63}$Ni. The separation zone of the employed instrument is 8 cm long; in all of the tests the electric field in the separation zone is equal to 128 V/cm.

EXAMPLE 1

Two IMS analyses are carried out on hydrogen samples. A first test is carried out at 80° C. according to the preferred embodiment of the method of the invention, that is, by using argon as the drift gas and a ratio of 16 between the flow rate of argon and that of the hydrogen sample. The sample gas in the test is hydrogen to which, by means of a calibration system based on mass flowmeters, 5 ppb of nitrogen and 10 ppb of $CO_2$ are added as intentional impurities. This sample further contains a few ppb of water, which represent a practically ineliminable base. The results of the test are shown in the graph in FIG. 1 as curve "a" (thin line in the figure). As a comparison, this graph also shows the results of a second test, carried out under the same conditions but on a hydrogen sample to which no $CO_2$ has been added (curve "b", thick line).

EXAMPLE 2

The tests of Example 1 are repeated using a ratio of 8 between the flow rate of argon and that of the hydrogen sample. The results of the analysis of hydrogen containing 10 ppb of $CO_2$ are shown in the graph in FIG. 2 as curve "c" (thin line), whereas the results of the test carried out on hydrogen without added $CO_2$ are shown in the same figure as curve "d" (thick line).

EXAMPLE 3 (COMPARATIVE)

The tests of Example 1 are repeated under conditions different from those according to the invention, that is, by employing pure hydrogen as the drift gas and a ratio between the flow rate of the drift gas and that of the sample gas of 12. Two tests are carried out, one with hydrogen containing 10 ppb of $CO_2$ and one with hydrogen without added impurity, but the results of the two analyses are completely superimposed in the only curve shown in the graph in FIG. 3.

EXAMPLE 4

Two IMS analyses are carried out on nitrogen samples. A first test is carried out at 110° C. according to the preferred embodiment of the method of the invention, that is, using argon as the drift gas and a ratio of 5.7 between the flow rate of argon and that of the nitrogen sample. The sample gas is prepared, using the same the calibration system of Example 1, by adding to nitrogen 15 ppb of oxygen as an intentional impurity; in this case the sample also contains a few tenths of ppb of water which cannot be eliminated. The results of this test are shown in the graph in FIG. 4 as curve "e" (thin line). The test is then repeated with nitrogen without added $O_2$ and the results are shown in the same figure as curve "f" (thick line).

EXAMPLE 5

The tests of Example 4 are repeated using a ratio of 1 between the flow rate of argon and that of nitrogen. The results of the test on nitrogen with added $O_2$ are shown in the graph in FIG. 5 as curve "g" (thin line), whereas the results of the test carried out on nitrogen without added $O_2$ are shown in the figure as curve "h" (thick line).

EXAMPLE 6 (COMPARATIVE)

The tests of Example 4 are repeated under conditions different from those according to the invention, that is, by employing pure nitrogen as the drift gas and a ratio between the flow rate of the drift gas and that of the sample of gas to be analyzed of 2.5. The results of the test on nitrogen with added $O_2$ are shown in the graph in FIG. 6 as curve "i" (thin line), whereas the results of the test carried out on nitrogen containing no $O_2$ are shown in the same figure as curve "l" (thick line).

EXAMPLE 7

An IMS analysis is carried out on an oxygen sample. The test is carried out at 80° C. according to the preferred embodiment of the invention method, by using argon as drift gas and a ratio of 1 between the flow rate of argon and that of the oxygen sample. Using the calibration system of Example 1, 5 ppb of water are added to the oxygen. The test results are shown in a graph in FIG. 7.

EXAMPLE 8 (COMPARATIVE)

The test of Example 7 is repeated under conditions different from those according to the invention, that is, by employing an oxygen flow containing no impurities as the drift gas and a ratio between the flow rate of the drift gas and that of the gas to be analyzed of 1. The results of the test are shown in the graph in FIG. 8.

Figure 1:
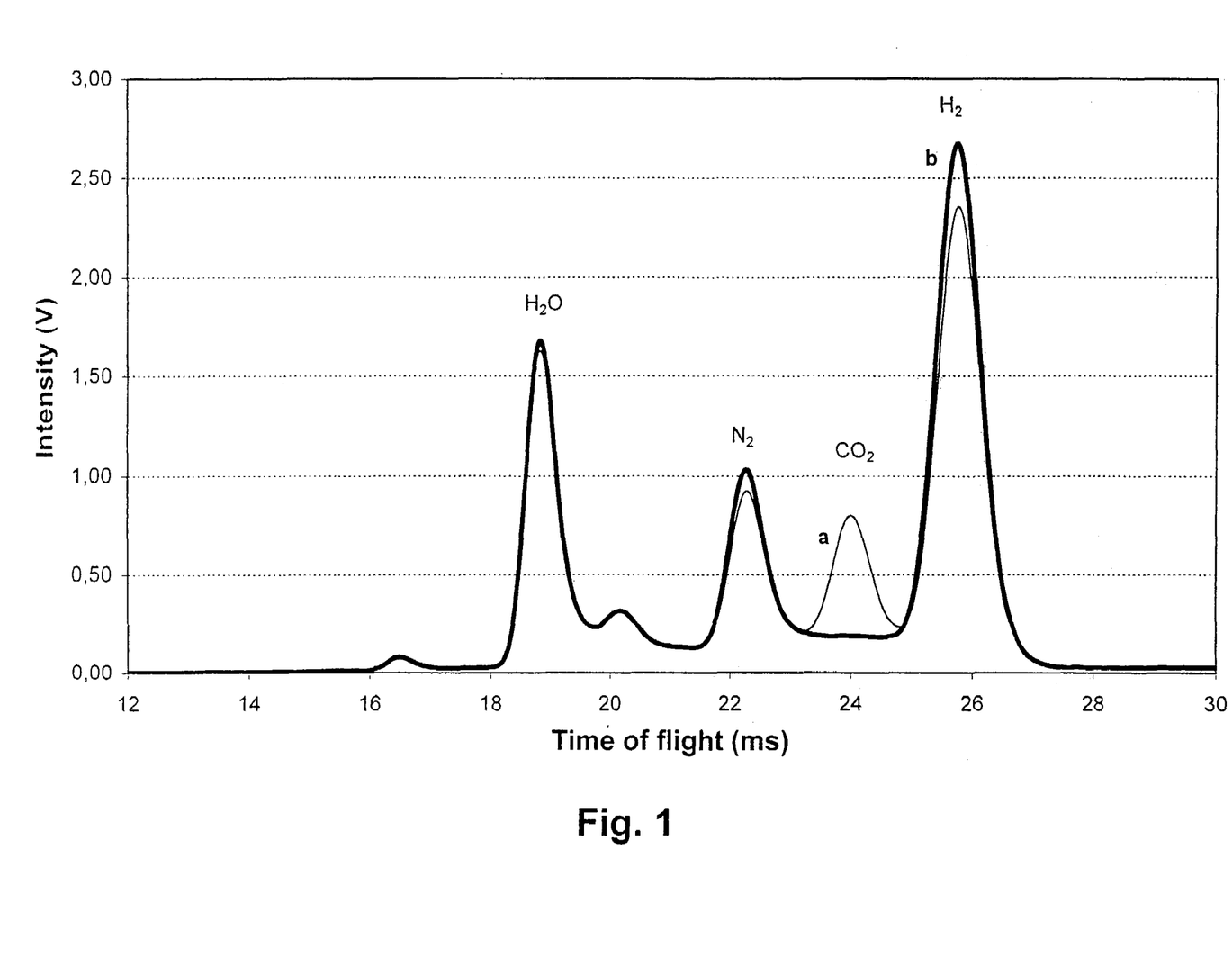
FIG. 1 is a graph of time of flight vs. intensity for the analysis of hydrogen according to one embodiment of the invention.
Figure 2:
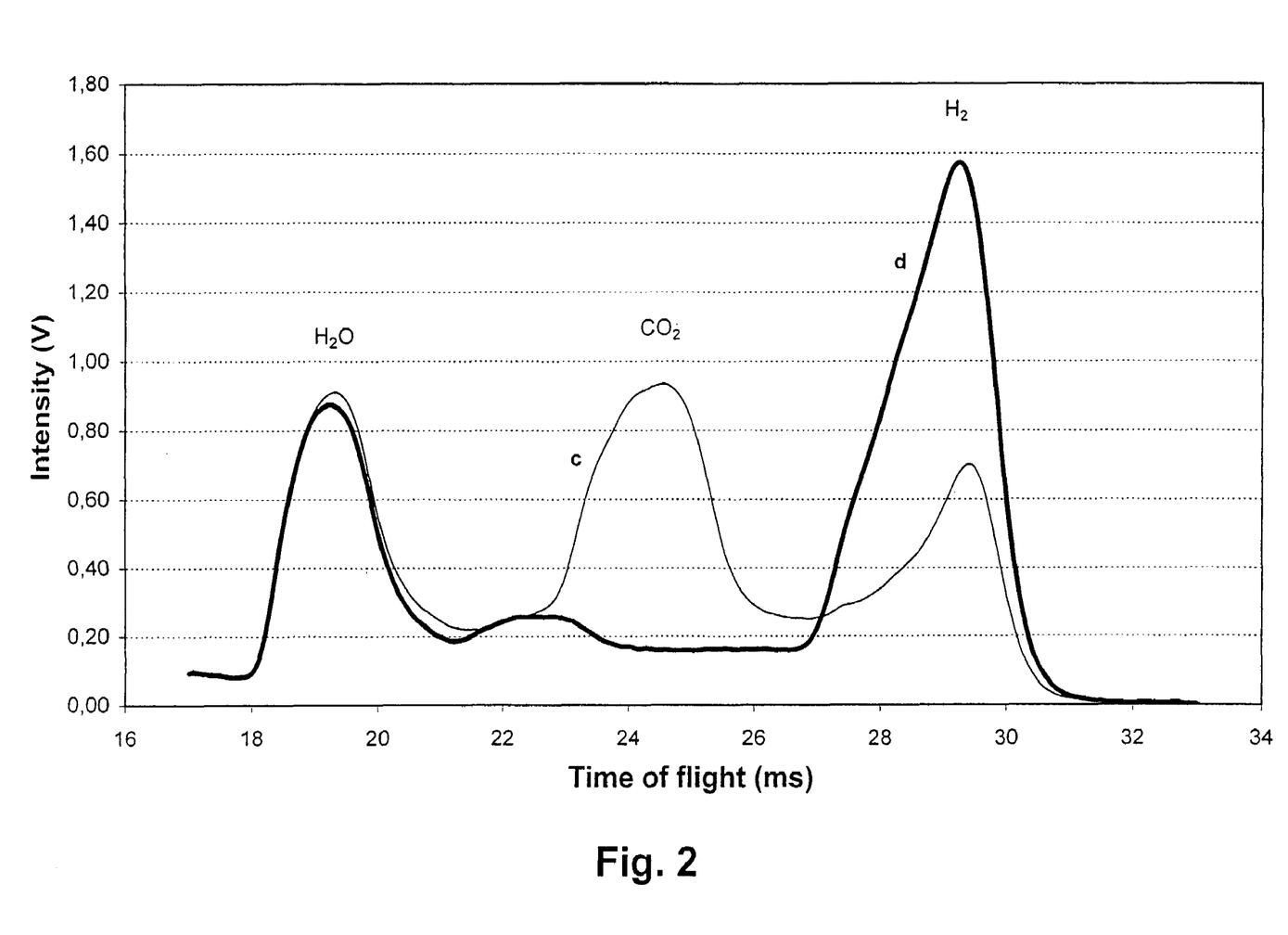
FIG. 2 is a graph of time of flight vs. intensity for the analysis of hydrogen according to a second embodiment of the invention.
Figure 3:
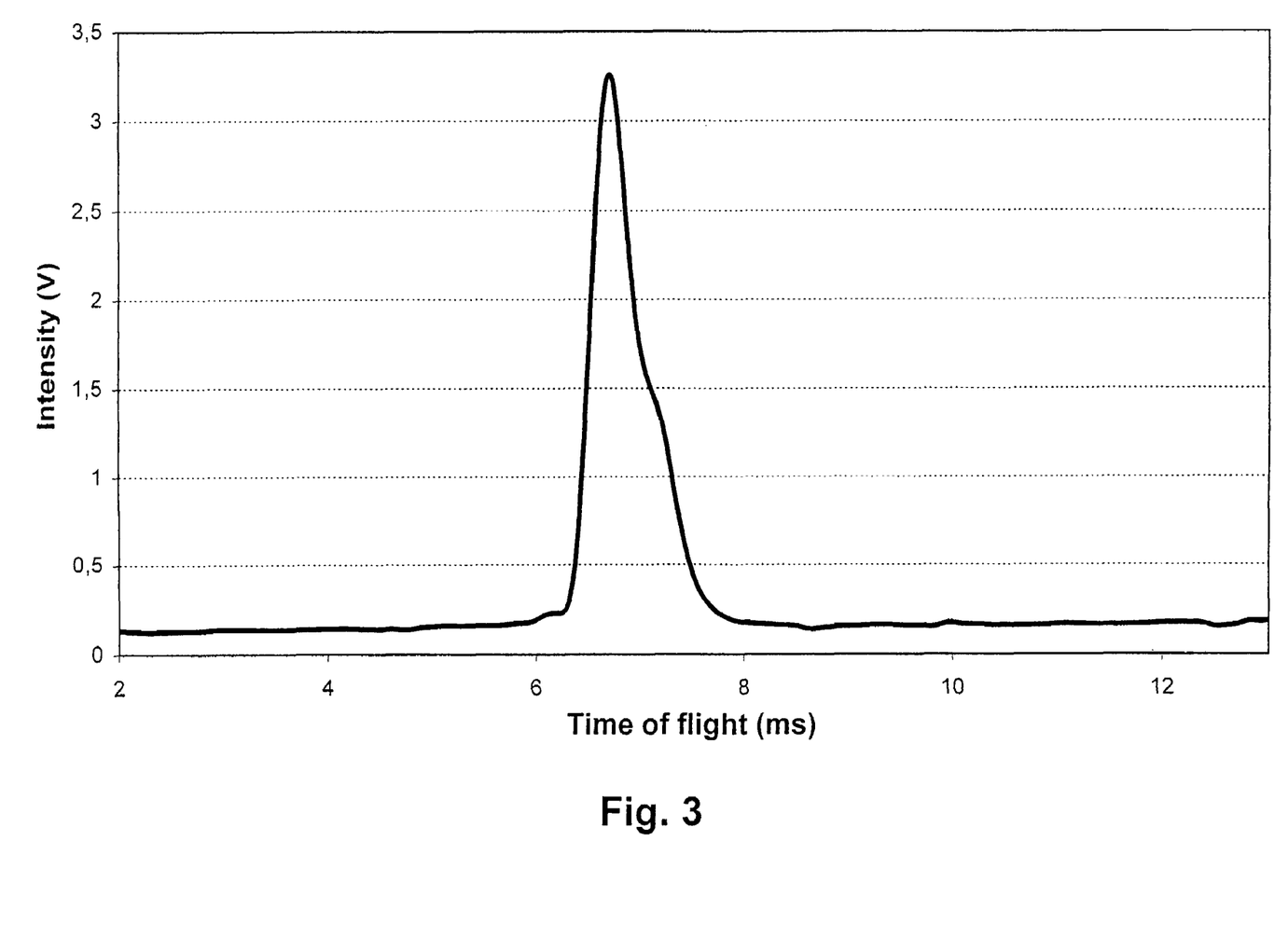
FIG. 3 is a graph of time of flight vs. intensity for the analysis of hydrogen according to a prior art method.

The results of the analyses of impurities in hydrogen are summarized in FIGS. 1–3. The times of flight in the various figures are different because changing the drift/sample flow rate ratio also modifies the clustering of ions and, consequently, the velocities of motion of cluster ions in the separation zone.

FIG. 1 refers to analyses run according to the preferred embodiment of the invention, that is, argon as the drift gas and a ratio between the flow rates of drift and sample gases in the preferred range. Curve "a" in FIG. 1 is relevant to the analysis of a sample of hydrogen containing $CO_2$ and nitrogen, whereas curve "b" is relevant to the analysis of a similar sample without $CO_2$. From comparing these two curves, it is possible to conclude that the analysis carried out according to the preferred embodiment of the invention is able to reveal the different impurities as well as distinct peaks, each one easily identifiable, whose areas (correlated to the concentration of the impurity) can be easily determined.

FIG. 2 shows two more curves, still obtained according to the invention (argon as drift gas) but in a less preferred embodiment thereof, that is, with a ratio between flow rates of drift and sample gases of lower than 10. Again, one test is carried with hydrogen containing 10 ppb of $CO_2$ and 5 ppm of $N_2$, and the second one with hydrogen containing no $CO_2$. From the curves obtained in these two cases (respectively "c" and "d"), it is observed that in the case of the sample containing only nitrogen, the shape of the peak relative to this gas is less defined than in the curves in FIG. 1, and by adding one impurity, $CO_2$, the peaks of $CO_2$ and of $N_2$ are superimposed. Under these conditions it is still possible to carry out the analysis, but with greater difficulties in the deconvolution of the peaks and in the quantitative calculation of the concentration of impurities.

Finally, FIG. 3 relates to analyses carried out according to the standard modality of the prior art, that is, using hydrogen as the drift gas. As it is easily observed, this mode of operating leads to a spectrum essentially formed of one single peak, in which it is impossible to recognize the presence of different species. Obviously, under these conditions, both the qualitative and the quantitative analyses of the different impurities are impossible.

Similarly, in the analysis of nitrogen (FIGS. 4–6), the use of argon as the drift gas allows one to obtain a spectrum having separated peaks.

Figure 4:
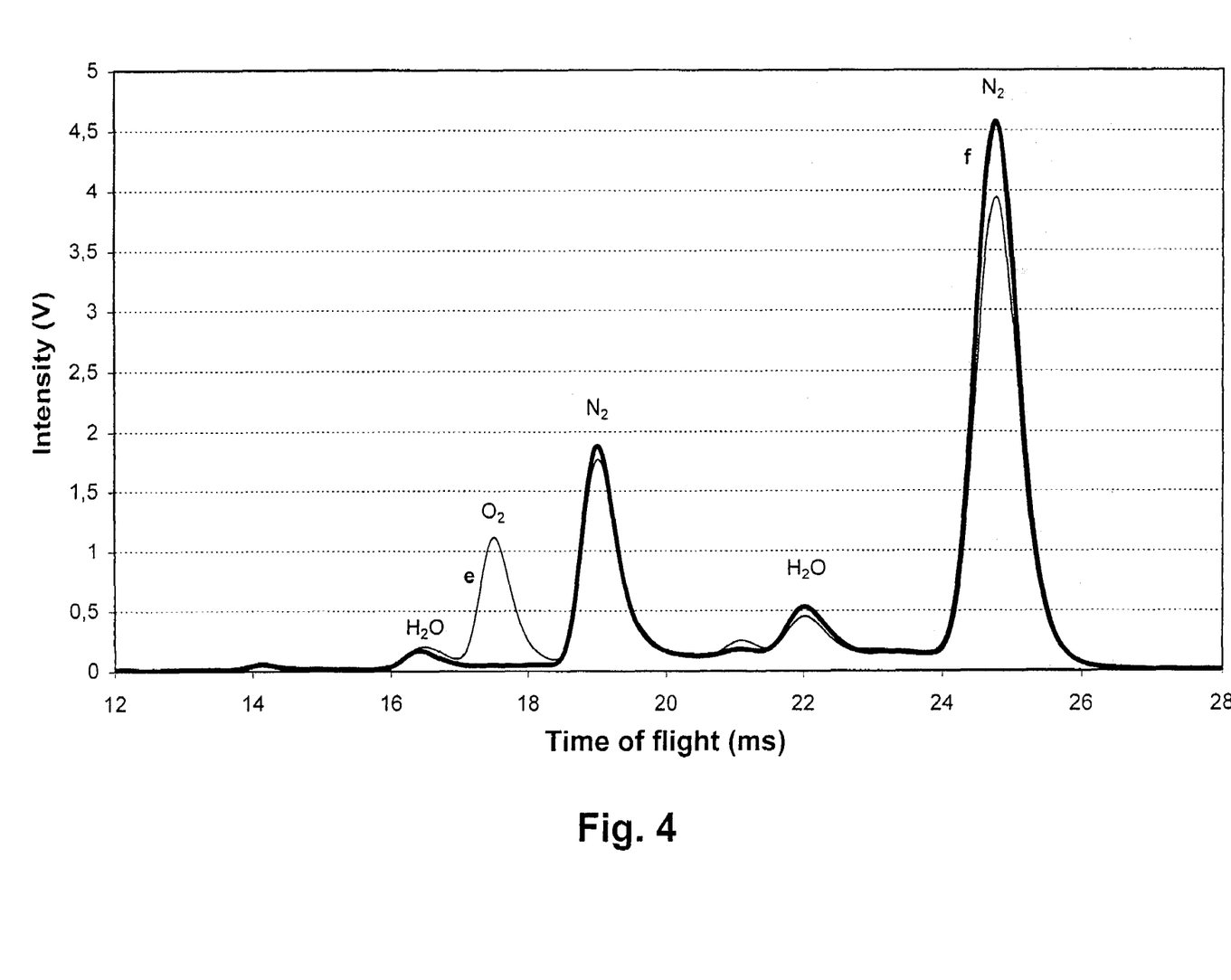
FIG. 4 is a graph of time of flight vs. intensity for the analysis of nitrogen according to one embodiment of the invention.

FIG. 4 relates to analyses carried out according to the preferred embodiment of the invention, that is, with a ratio between the flow rate of drift gas and sample gas of higher than 5. Curves "e" and "f" respectively show the analyses of a nitrogen sample containing $O_2$ as intentionally added impurity and of a sample containing no $O_2$. In this case, there are also peaks present which can be ascribed to water present as an ineliminable base in concentration of a few ppb. As can be seen, the peak for the impurity $O_2$ in curve "e" is well isolated and defined, thus allowing an easy determination of the concentration of this impurity.

Figure 5:
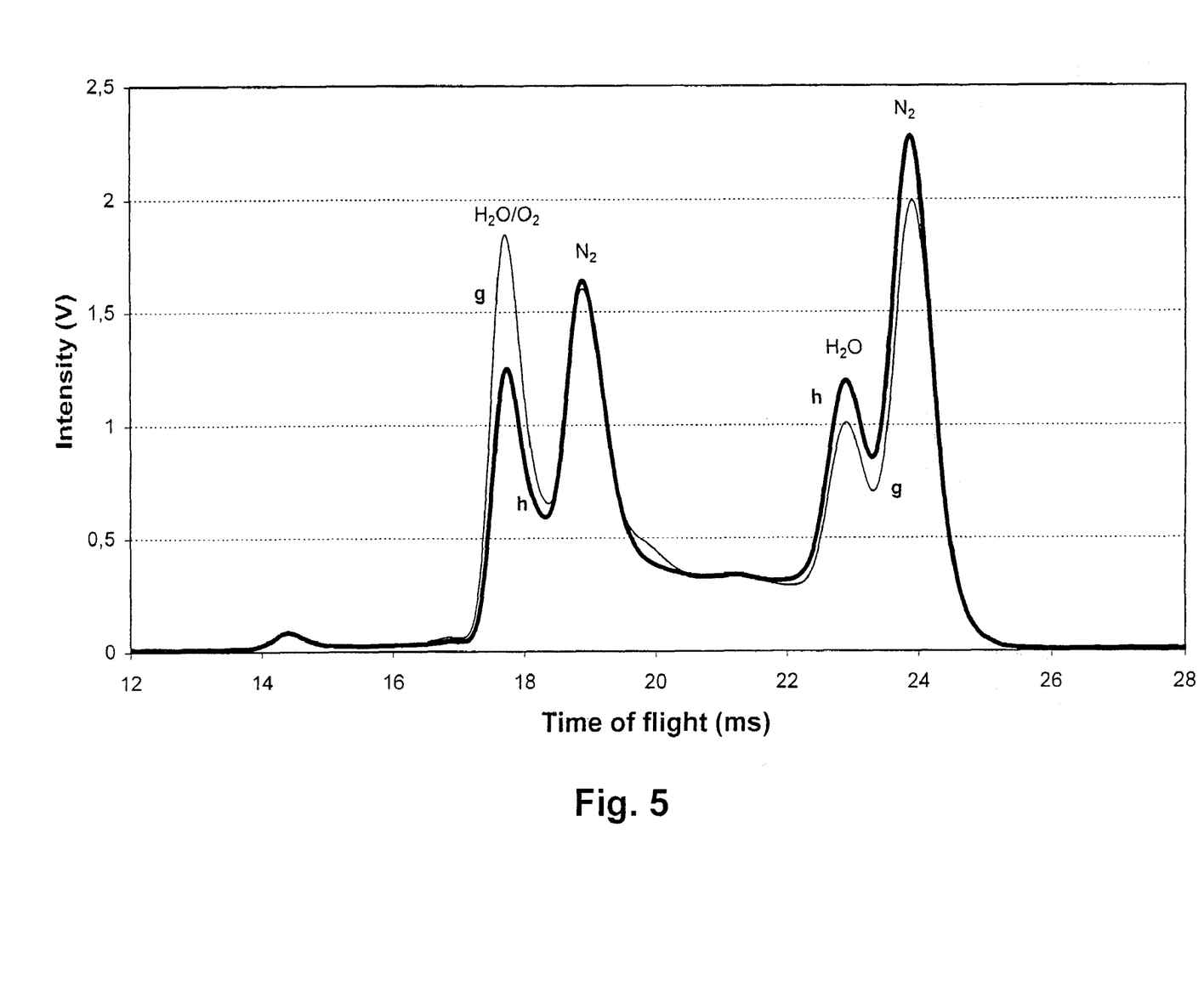
FIG. 5 is a graph of time of flight vs. intensity for the analysis of nitrogen according to a second embodiment of the invention.

FIG. 5 refers to analyses carried out by still operating according to the invention (argon drift) but in a less preferred embodiment thereof (using a ratio between flow rate of drift and of sample gas of lower than 5). The peaks of oxygen and water are superimposed. It is still possible to determine the quantity of oxygen, but in this case, there is a difference with respect to the quantity of water (whose concentration can be measured from the peak at about 23 ms).

Figure 6:
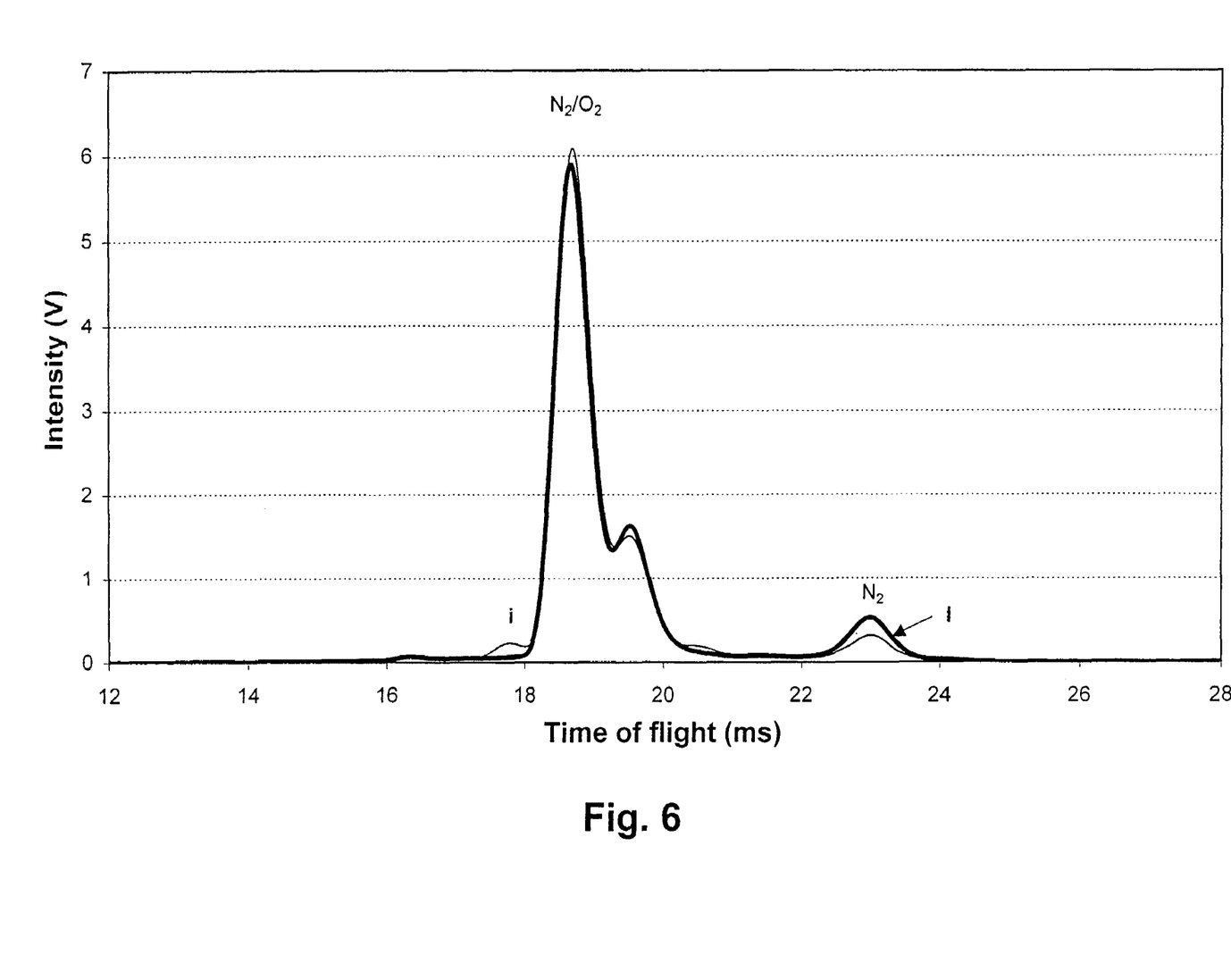
FIG. 6 is a graph of time of flight vs. intensity for the analysis of nitrogen according to a prior art method.

The curves in FIG. 6 are obtained by operating according to the method of the prior art, that is by using pure nitrogen as the drift gas. Curves "i" and "l", representing respectively nitrogen containing $O_2$ and nitrogen containing no $O_2$, are almost completely superimposed and present a smaller number of peaks. Under these conditions, it is not possible to correctly evaluate the area of the oxygen peak, and the analysis of this impurity is practically impossible.

Figure 7:
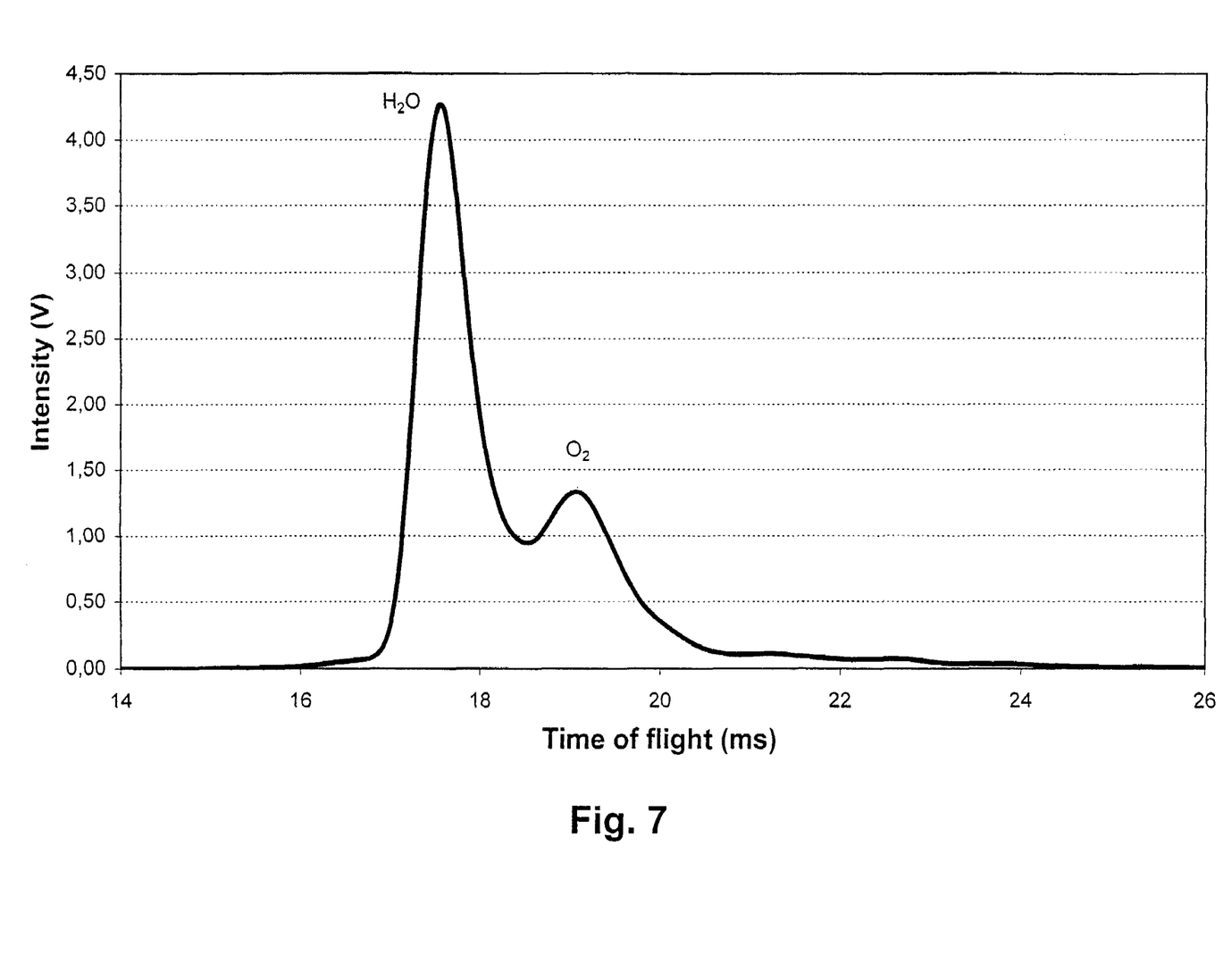
FIG. 7 is a graph of time of flight vs. intensity for the analysis of oxygen according to one embodiment of the invention.
Figure 8:
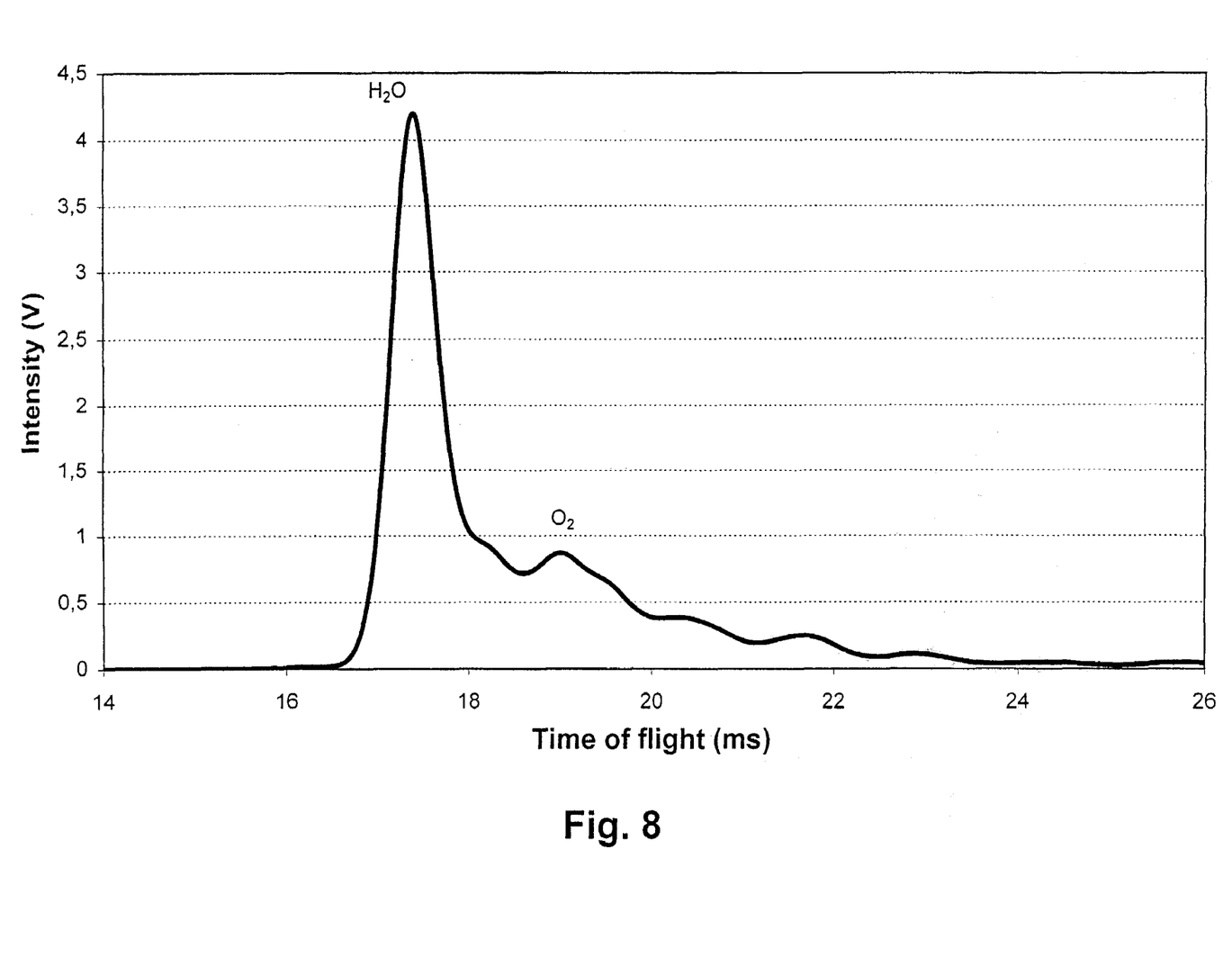
FIG. 8 is a graph of time of flight vs. intensity for the analysis of oxygen according to a prior art method.

Finally, FIGS. 7 and 8 illustrate the analyses of traces of water in oxygen samples according to the invention and to the prior art. The graph reported in FIG. 7 (use of argon as the drift gas, according to the invention) shows two neat and rather well separated peaks. On the other hand, the graph of FIG. 8 (use of oxygen as the drift gas, prior art) shows, in the zone between 19 and 23 ms, a series of spurious signals which complicates the deconvolution of the graph, introducing a possible source of errors in the quantitative analysis.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for measuring a concentration of impurities in a gas to be analyzed selected from the group consisting of hydrogen and oxygen using ion mobility spectrometry; the method comprising employing as a counterflow gas in a separation zone of an ion mobility spectrometer pure argon or a mixture of argon and the gas to be analyzed, wherein the mixture contains no impurities and is an argon/hydrogen or argon/oxygen mixture comprising at least 50% by volume of argon based on a total volume of the mixture; and:
   (a) when the gas to be analyzed is hydrogen, a ratio between a flow rate of argon or the argon/hydrogen mixture and a flow rate of the hydrogen is at least 10; or
   (b) when the gas to be analyzed is oxygen, a ratio between a flow rate of argon or the argon/oxygen mixture and a flow rate of the oxygen is between 0.3 and 1.5 or between 6 and 10.

2. The method according to claim 1, wherein the gas to be analyzed is hydrogen and the ratio is between 15 and 25.

3. The method according to claim 1, wherein the gas to be analyzed is oxygen and the ratio is equal to about 0.5 or about 8.

* * * * *